United States Patent
Franzen

(10) Patent No.: US 7,442,921 B2
(45) Date of Patent: Oct. 28, 2008

(54) PROTEIN PROFILES WITH ATMOSPHERIC PRESSURE IONIZATION

(75) Inventor: Jochen Franzen, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 411 days.

(21) Appl. No.: 11/256,648

(22) Filed: Oct. 21, 2005

(65) Prior Publication Data
US 2006/0097143 A1    May 11, 2006

(30) Foreign Application Priority Data
Oct. 25, 2004    (DE) ................ 10 2004 051 785

(51) Int. Cl.
B01D 59/44    (2006.01)
H01J 49/00    (2006.01)

(52) U.S. Cl. .............. 250/282; 250/290; 250/288; 250/292; 250/293; 250/284; 250/287; 250/424; 702/23; 702/27; 702/104; 435/6; 435/7.1; 435/7.23; 435/174

(58) Field of Classification Search .......... 250/282, 250/290, 288, 292, 293, 284, 287, 424; 702/23, 702/27, 104; 435/6, 7.1, 7.23, 174
See application file for complete search history.

(56) References Cited

U.S. PATENT DOCUMENTS

| | | | |
|---|---|---|---|
| 5,373,156 A | 12/1994 | Franzen | |
| 5,663,561 A | 9/1997 | Franzen et al. | |
| 5,965,884 A | 10/1999 | Laiko et al. | |
| 6,683,300 B2 * | 1/2004 | Doroshenko et al. | 250/288 |
| 6,707,037 B2 * | 3/2004 | Whitehouse | 250/288 |
| 7,022,981 B2 * | 4/2006 | Kato | 250/288 |
| 2003/0052268 A1 | 3/2003 | Doroshenko et al. | |
| 2004/0089802 A1 | 5/2004 | Kato | |

FOREIGN PATENT DOCUMENTS

| | | |
|---|---|---|
| DE | 42 02 123 A1 | 1/1992 |
| DE | 196 08 963 A1 | 3/1996 |
| DE | 196 17 011 A1 | 4/1996 |
| DE | 196 08 963 C2 | 10/1996 |
| DE | 199 34 173 A1 | 7/1999 |
| DE | 199 34 173 A1 | 1/2001 |
| DE | 10 2004 002 729 A1 | 1/2004 |
| EP | 0 964 417 A2 | 12/1999 |
| EP | 0 964 427 A2 | 12/1999 |
| EP | 0 966 022 A2 | 12/1999 |
| GB | 2 299 445 A | 3/1996 |
| GB | 2 310 950 A | 9/1997 |
| WO | WO 98/00224 A1 | 1/1998 |
| WO | WO 99/38185 A2 | 7/1999 |
| WO | WO 03/102508 A1 | 12/2003 |
| WO | WO 2004/030024 A2 | 4/2004 |

* cited by examiner

*Primary Examiner*—Jack I. Berman
*Assistant Examiner*—Meenakshi S Sahu
(74) *Attorney, Agent, or Firm*—Law Offices of Paul E. Kudirka

(57) ABSTRACT

The invention relates to the acquisition of mass spectra of complex protein mixtures, often called protein profiles, for example to search for biomarkers which indicate stress situations, or to identify microbes. Up to now protein profiles have been acquired using ionization by matrix-assisted laser desorption with high detection sensitivity in linear time-of-flight mass spectrometers, but these display very poor mass resolution and a very poor reproducibility of the mass values. The invention provides methods which produce surprisingly similar mass spectra, but with far higher mass resolution and mass accuracy. Ionization takes place outside the vacuum at ambient pressure, preferably by means of laser desorption and CI post-ionization. Analysis of the ions takes place in a high-resolution mass spectrometer, for example a reflector time-of-flight mass spectrometer with orthogonal ion injection.

13 Claims, 1 Drawing Sheet

PROTEIN PROFILES WITH ATMOSPHERIC PRESSURE IONIZATION

FIELD OF THE INVENTION

The invention relates to the acquisition of mass spectra of complex biomaterial mixtures, e.g. protein profiles, for example to search for biomarkers which indicate stress situations of the spender of the biomaterial, or to identify microbes.

BACKGROUND OF THE INVENTION

Up to now protein profiles have been acquired in mass spectrometry using ionization by matrix-assisted laser desorption (MALDI) with high detection sensitivity in linear time-of-flight mass spectrometers, but these display very poor mass resolution and a very poor reproducibility of the mass values. A recently devised method permits very easy, and largely automated, identification of microbes, especially bacteria, by mass spectrometry. In this method, small quantities of microbes are first taken from a colony grown overnight on a nutrient medium and transferred to a mass spectrometric sample support plate. The microbes are then sprinkled with a solution of a customary matrix substance for ionization using matrix-assisted laser desorption (MALDI). This solution penetrates into the microbial cells and destroys them during the crystallization of the matrix material in the subsequent drying process. Proteins and peptides, and possibly other analyte substances of the cell, are integrated into the matrix crystals. The dry sample with the matrix crystals is then bombarded with pulsed flashes of laser light in the vacuum of a time-of-flight mass spectrometer, creating pulses of ions of the analyte substances, which can then accelerated and be measured in the time-of-flight mass spectrometer. The mass spectrum is the profile of the measured ion current values of these peptide ions, protein ions and other analyte ions of the microbial material. This profile is very characteristic of the microbe species concerned. It is even possible to distinguish between substrains of microbes because their composition of proteins, defined by the genes in a one-to-one translation without much modifications, is very characteristic. Even small changes in the genes generate proteins of slightly different masses detectable by mass spectrometry. The identification appears to be extremely reliable, as far as current analyses have shown. It does not require individual identification of the proteins involved.

In a similar way, protein profiles are acquired in the search for so-called "biomarkers". Biomarkers are indicators of stress situations in organisms, whether diseases, chemical and pharmacological stress, ageing, physical stress caused by heat or impact, or stress with other causes. Biomarkers are represented as up or down regulated proteins caused by the stress. Biomarkers are read out from mass spectra of the protein profile samples obtained from body fluids or tissue homogenates. The samples can contain either all proteins or only extracted sub-quantities of proteins. As the protein profiles themselves usually display some fluctuations in signal intensity, in most cases a statistical evaluation is required, for which mass spectra of cohorts of "normal samples" or "healthy samples" (samples from healthy individuals) are compared with mass spectra from other cohorts of "stress samples" or "disease samples" (samples from diseased individuals). The biomarkers are obtained by statistical evaluation of the ion signals in the mass spectra. These biomarkers can be individual proteins which are over-expressed or under-expressed to a statistically significant degree, or they can be characteristic intensity patterns of relatively large numbers of proteins, i.e. the biomarkers can only be expressed as mathematical or logical expressions containing intensities of a variety of ion signals.

For these applications, mass spectra are acquired at present in linear time-of-flight mass spectrometers because of their particularly high detection sensitivity, even though the mass resolution and mass accuracy of the spectra from time-of-flight mass spectrometers with reflectors are incomparably superior. In reflector mode, however, only about a twentieth of the ion signals appear, and the detection sensitivity is inferior by several orders of magnitude. The inadequate quality of the mass spectra in time-of-flight mass spectrometers operated in linear mode is partially due to the formation process for ions by matrix-assisted laser desorption in vacuum (vacuum-MALDI). Vacuum-MALDI delivers ions of widely differing initial velocity distributions and differing mean initial energies The processes during ionization of the analyte substances in the laser-induced vaporization cloud are not easily reproducible; they depend greatly on structural inhomogeneities of the microcrystalline sample after it has been prepared. Furthermore, the uneven thickness of the sample after its preparation causes the formation of ions at differing initial potentials, with the result that they pass through varying potential differences, and therefore absorb slightly different energies, according to the location where they were formed. These effects influencing the flight times of the ions can be partly eliminated, for example by means of delayed acceleration, but they cannot all be corrected simultaneously. On account of the change in the flight times of the ions from spectrum to spectrum, the mass scales of the spectra are distorted because these are calculated from the flight times using the calibration curve, which is determined once.

The acquisition of mass spectra with time-of-flight mass spectrometers generally requires a very large number of individual spectra, which are usually added together, measuring value by measuring value, to form sum spectra. The ions for the individual spectra are generated by a laser shot each. This procedure of generating sum spectra is made necessary by the low measuring dynamics in the individual spectrum. At least about 50, and in some cases even 1,000 or more, individual spectra are acquired; in general, a sum spectrum consists of several hundred individual spectra. By adding up spectra with different mass values for identical substances the resolution of the mass spectrum is greatly deteriorated.

In the linear operating mode of a time-of-flight mass spectrometer, it is possible to detect not only the stable ions, but also the fragment ions from so-called "metastable" decompositions of the ions, and even neutral particles that are formed from the ion decompositions along the way. All these fragment ions and neutral particles which have resulted from a single parent ion species have the same velocity as the parent ions and therefore reach the ion detector at the same time. In the applications described above, this gives a ten-fold to hundred-fold detection sensitivity. For these applications, the energy of the desorbing and ionizing laser is raised, thereby increasing the ion yield, but also their instability. This increased detection sensitivity is of such decisive importance for many applications that the disadvantages of linear operation of time-of-flight mass spectrometers described above are more or less accepted.

These decompositions of the ions always add to the inferiority of the mass resolution. When an ion decomposes, a small excess of internal energy is always released, which is transferred to the two fragments of the ion as kinetic energy. Depending on the direction of the decomposition in relation to the direction of flight, the particles may be slightly accelerated or slightly decelerated. This results in a broader distribution of the flight times of particles that have the same parent ion mass, and that in turn reduces the mass resolution. This reduction in resolution is thus inseparably connected with the increase in detection sensitivity, and cannot, in principle, be removed. The mass resolutions are only around R=400 to R=1,000.

The non-reproducibility of the mass scale described above means that no easily comparable mass spectra are obtained. It is difficult, for example, to create a good reference spectrum library for identifying microbes on the basis of their protein profiles. Spectra of the same microbes from different sample preparations do not match exactly, but display apparently different mass values for what are actually identical proteins. Deviations of up to one percent of the mass value have been observed.

The non-reproducibility of the mass scales of linear TOF mass spectra is particularly bothering if promising biomarker patterns have been found, validated by thousands of samples, and now should be used for diagnostic assays for diseases. There is a large field of future applications of mass spectrometry in medicine. In medicine, however, very strong rules apply to the reproducibility of measuring results. The application of linear time-of-flight mass spectrometers without safe methods to correct for distorted mass scales or without better reproducibility will presumably not permitted by validating organizations.

In the applications described above, mass spectra up to high mass ranges of, for example, 20,000 Daltons are measured. For reasons of low mass resolution, as mentioned, the isotope groups, which consist of several ion signals that differ by one Dalton respectively, cannot be resolved in major parts of the mass spectrum. Therefore, only the envelopes of the isotope groups are measured, a fact that makes mass determination and a corresponding calibration even more difficult. Furthermore, protein profile spectra in particular are very rich in ion signals, with many ion signal overlaps, which greatly impedes the comparison of patterns. The protein profile spectra usually contain the ion signals of several hundred different proteins.

Time-of-flight mass spectrometers with reflectors have a very much better mass resolving power, in particular because no fragment masses contribute to the mass spectrum. Unfortunately, this means that protein profile spectra, whether for searching for biomarkers or for identifying microbes, cannot be acquired in reflector mode. The mass spectra in reflector mode only show around a twentieth of the ion signals, albeit with far better mass resolution, but the wealth of mass spectra obtained with the linear mode, and the associated capacity for biomarker search or microbe identifications, is lost. Furthermore, the detection sensitivity is drastically reduced, although mass-resolved mass spectra generally display higher detection sensitivity on account of the better signal-to-noise ratio.

There have been made trials to replace vacuum MALDI by atmospheric pressure electrospray ionization in combination with high resolution mass spectrometers for biomarker searching. But the generation of large amounts of doubly, triply and even quadruply charged ions creates much too complex spectra; and the richness of the spectra with ion signals does no longer permit to distinguish between singly and multiply charged ion species. MALDI, in contrast, has the advantage of yielding singly charged ions only. The use of electrospray ionization in combination with a separation of the substances of the complex mixtures in biomaterial by chromatography or capillary electrophoresis does in principle work, but requires much longer measuring times per sample (hours instead of seconds), and increases the amount of data to be handled by factors of thousands.

In most raw biomaterial samples like blood, plasma, homogenized tissue, spinal liquid and many others, the complexity of proteins is even too high for linear mode time-of-flight mass spectra generated by vacuum-MALDI. Raw biomaterial samples usually contain thousands of proteins. There are, however, solutions to this problem. The complexity of the biomaterial can be reduced by several methods, e.g. by broadband extraction of subsets of proteins with magnetic beads that have been activated at their surfaces to bind groups of proteins by different types of affinity. Magnetic beads are available with different degrees of hydrophobicity, with cation and anion exchange phases, with different immobilized metals, or even with proteins acting as ligands, e.g. antibodies. Each of these types of magnetic beads can reduce the extract to several hundred types of proteins, thereby reducing the complexity considerably.

Beside vacuum-MALDI, there have been also different approaches to generate ions by MALDI at atmospheric pressure (AP-MALDI). The ionization can take place, just as in vacuum-MALDI, by means of protonation by matrix substance ions which occur in the plasma of the laser evaporation cloud. Such "normal" AP-MALDI at atmospheric pressure with protonation by the matrix substance is proposed in the patents U.S. Pat. No. 5,965,884 (V. V. Laiko and A. L. Burlingame) and EP 0 964 427 A2 (J. Bai et al.). This ionization at atmospheric pressure seems to have a higher yield of analyte ions because the analyte molecules and the matrix substance ions are kept together for longer time by the inert gas than is the case in the vacuum, and therefore display a better protonation yield. On the other hand, the introduction of the ions into the vacuum causes the vast majority of the ions to get lost, with the result that this method has a lower overall detection sensitivity than a method with production of vacuum-MALDI ions in vacuum. The yield of analyte ions generated in vacuum-MALDI amounts to about a ten-thousandth of the evaporated analyte molecules; at atmospheric pressure, the yield of evaporated analyte molecules of AP-MALDI is assumed to amount to roughly a thousandth.

In contrast to this commercially available AP-MALDI, the patent U.S. Pat. No. 5,663,561 (J. Franzen and C. Köster) proposes to avoid the background created by the usual matrix substances by the use of decomposable matrix substances and to greatly increase the yield of analyte ions at atmospheric pressure by post-ionization of the analyte molecules. As only around a thousandth of the analyte molecules is ionized by the usual AP-MALDI process, there is a large potential for increasing the detection sensitivity here. The post-ionization can be carried out by photo ionization using a UV lamp, for example, or by chemical ionization, which produces a particularly high yield of analyte and is therefore preferred.

Chemical ionization (CI) usually starts with an electron source generating a very large number of electrons, which in turn generate many primary ions of an inert gas which can be nitrogen, for example. Usually suitable substances to form reactant ions, sometimes called "mediators", such as low amounts of water, methane, butane, or even xylene, are added to the inert gas, The inert gas ions then react immediately (within some ten nanoseconds) with the water molecules, forming $OH_3^+$, $O_2H_5^+$ and higher protonated water clusters. Within microseconds, these water cluster ions form protonated methane clusters or reactant ions from the other mediator substances. The protonated reactant ions are then available for the protonation of the analyte molecules. By this rather complicated reaction chain reactant ions are formed which react with the analyte ions in such a manner that virtually no fragment ions occur during protonation of the analyte molecules. Chemical ionization (CI) is therefore termed "soft". Only singly charged non-fragmented ions are generated by this process.

In APCI (atmospheric pressure chemical ionization), corona discharges at the tip of corona discharge needles under high voltage or $^{63}$Ni beta radiation emitters can produce a large amounts of reactant ions which in turn may ionize the majority of the analyte molecules. The $^{63}$Ni beta radiation emitter, in the form of a ring-shaped foil with a diameter of approximately one centimeter and a width of two millimeters can be easily mounted around the sample gas volume as known from ion mobility spectrometry.

In another type of atmospheric pressure ionization (API), the reactant ions can, however, already have been added to the inert gas when the latter is fed to the sample as a purging flow, as also described in the patent U.S. Pat. No. 5,663,561, referred to above. The sample is then desorbed by laser shots into the flowing inert gas. But in this case, different flows of gases have to mix, the desorption plume on one hand, and the inert gas with the reactant ions on the other hand. The expanding desorption plume first pushes aside the inert gas without mixing. Because mixing at atmospheric pressure takes time in the order of many milliseconds even for small volumes, this procedure is much less efficient than expected.

Electron beams can also be generated by photon bombardment of suitable surfaces with an adequately low work function. The surface can be bombarded with UV radiation from a UV lamp or a UV laser, either continuously or in pulses. A withdrawal potential of several kilovolts draws the electrons away from the surface and accelerates them to a level where they are able to generate large quantities of inert gas ions. These ions can build up the chain of reactant ions.

SUMMARY OF THE INVENTION

The invention provides a method by which the vacuum-MALDI mass spectra of complex analyte mixtures from the linear mode of time-of-flight mass spectrometers, with their wealth of ion signals, can be reproduced with substantially better mass resolution and mass accuracy.

The invention is based on the surprising observation that the mass spectra of protein ions which are produced from complex protein mixtures by means of laser bombardment at atmospheric pressure (AP-MALDI) and measured in a reflector type time-of-flight mass spectrometer with orthogonal ion injection (OTOF) do, under certain circumstances, reflect the entire wealth of ion signals that are seen in mass spectra of the same samples with conventional methods in the linear mode (linear TOF); in stark contrast to the rather meager mass spectra obtained from these samples in the reflector time-of-flight mass spectrometer (OTOF) when the process of ionization by matrix-assisted laser desorption in vacuum is used.

The invention therefore combines a favorable type of atmospheric pressure ionization of desorbed molecules from biomaterial with high resolution mass spectrometry, for example by a reflector time-of-flight mass spectrometer with orthogonal ion injection (OTOF). To keep the richness of information, continuous or quasi-continuous desorption by light from pulse lasers, CW lasers, or even laser diodes are most favorable. This type of desorption can generate a continuously streaming rivulet of analyte ions in sufficiently low density for highly effective chemical or photon ionization. "Quasi-continuous desorption" is defined here as pulsed desorption with such a high pulse frequency that the desorption plumes, immediately damped by the surrounding inert gas and only slowly transported away, run into each other and form a continuous stream of desorbed analyte molecules. This process delivers a constant ion current to the mass spectrometer.

The ionization of the analyte molecules can be supported by matrix substances added to the sample as mediator substances. The mediator substances are desorbed together with the analyte molecules, and can serve in at least two ways in the ionization of the analyte molecules. In one way, the electrons from corona discharge tips or beta radiation emitters generate, by chemical ionization, protonated reactant ions from the mediator substances which, in turn, chemically ionize the analyte molecules. The other way uses mediator substances particularly suitable for photo ionization, carrying UV light absorbing chemical groups. These mediator substances are easily ionized by photo ionization, either from UV lamps or even from UV laser diodes. The mediator ions then chemically ionize the analyte molecules.

In addition to the mediator substances, matrix substances which decompose in the desorbing laser light, may be used in the sample preparation. This substance may serve to hold the analyte molecules separated from each other and allows to use a concentration of the mediator substance at optimum for the ionization purpose.

The invention not only generates signal-rich high-resolution mass spectra with accurate masses, but also offers other substantial advantages. Firstly, high-resolution mass spectrometers for external ion generation by electrospray are readily available commercially as fully developed systems. Secondly, laser desorption at atmospheric pressure is simple, and does not require the sample carrier plates to be introduced into the vacuum. The sample carrier plates are simply placed on a moving device, and the analysis can begin. This is a particular advantage for users in medical and microbiological circles who are not accustomed to using vacuum apparatuses.

BRIEF DESCRIPTION OF THE DRAWINGS

The above and further advantages of the invention may be better understood by referring to the following description in conjunction with the accompanying drawings in which.

DETAILED DESCRIPTION

Figure 1:
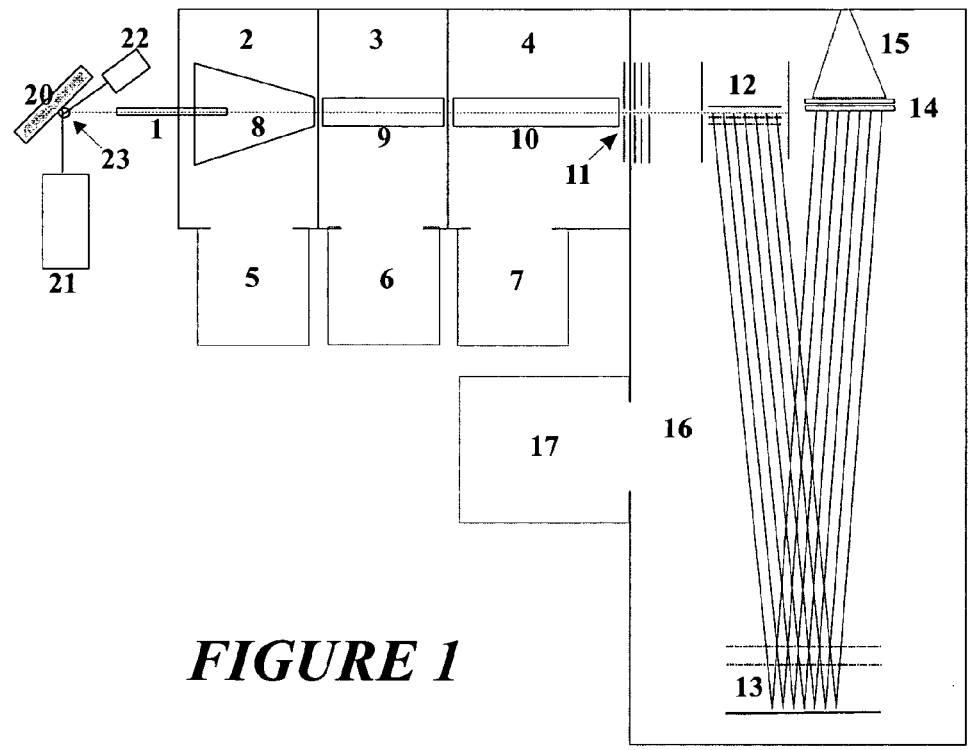
FIG. 1 presents a schematic view of a typical reflector type time-of-flight mass spectrometer with orthogonal ion injection as used also for electrospray ionization (1-17). In front of this spectrometer, a laser desorption ion source is mounted, with sample carrier (20), desorption laser (21), UV laser diode (22) for photo ionization of the mediator substances in the desorption plume (23), thus generating analyte ions.

The baffling similarity between vacuum-MALDI mass spectra in linear TOF instruments and special-type AP-MALDI mass spectra in reflector TOF mass spectrometers is not yet fully explained. It may be due to an immediate cooling of the metastable molecules generated in the generally harsh desorption process. The cooling at atmospheric pressure seems to take place very rapidly, within microseconds or shorter, by the ambient gas. The cooling seems to affect not only the thermal movement in the heated plasma of the desorption cloud, but also the internal energies of the ions and molecules, which are consequently no longer instable and do no longer decompose in the further process of analysis. For the success of the cooling process it seems to be required that the momentary plume of desorbed material is very small.

A particular embodiment of the invention consists in a method for acquiring mass spectra of complex analyte mixtures from biomaterial, the method comprising the following steps:
  (a) a high-resolution mass spectrometer has to be provided, preferably a reflector type time-of-flight mass spectrometer with orthogonal ion injection, which is capable to analyze ions generated outside the mass spectrometer at atmospheric pressure,
  (b) samples have to be prepared on a sample carrier whereby the samples contain at least the analyte mixtures,
  (c) sample molecules have to be desorbed from the sample carrier within an inert gas at atmospheric pressure outside the mass spectrometer,
  (d) reactant ions have to be created inside the plume of desorbed sample molecules; whereby the analyte molecules will be ionized by reactions with the reactant ions,
  (e) at least a part of the analyte ions have to be fed into the vacuum system of the mass spectrometer, and
  (f) high-resolution mass spectra of the analyte ion mixture have to be acquired.

For the creation of reactant ions inside the desorption plume, it is advantageous to add to the sample a type of matrix substance which can serve as mediator substance. The desorbed molecules of the mediator substance can be ionized into reactant ions by electrons which are shot with some kinetic energy into the desorption plume. The ionization of the mediator molecules may not be directly caused by the electrons, a chain of reactions starting from ionized inert gas may lead finally to the reaction ions. The electrons may be generated by beta radioactivity, by a corona discharge, or by a surface under irradiation with UV light to release electrons. Favorable mediators are crystalline substances in the molecular weight range from 120 to 200 Daltons. Some matrix substances used hitherto in vacuum-MALDI are excellent mediator substances for the purpose of creating reactant ions to ionize the analyte molecules.

Strong electron sources, such as corona discharges or $^{63}$Ni beta radiation emitters produce a large excess of reactant ions, which ionizes the majority of the analyte molecules. A $^{63}$Ni beta radiation emitter, in the form of a ring-shaped foil with a diameter of approximately one centimeter and a width of two millimeters can be easily mounted around the sample on the sample carrier so that, after a portion of the sample has been desorbed, chemical ionization can begin immediately even inside the desorption plume. In fact, with this arrangement the electrons are injected directly into the desorption plume, the reactant ions are generated inside the desorption plume and the protonation of the analyte molecules has a high yield.

In a slightly different method, the mediator substance molecules inside the desorption plume can be ionized to reactant ions by UV photo ionization. For this, the mediator substance should possess chemical groups (chromophores) which are capable to absorb the UV quanta. Substances which can be easily ionized by UV quanta are known to the specialist in the field. Most of the matrix substances used hitherto in MALDI processes are highly absorptive for UV quanta, because they are particularly selected by their UV absorptivity. The photons for the photo ionization may be generated by a UV lamps or by a UV laser diodes.

The sample on the sample carrier not only may contain some mediator substances beside the complex analyte mixture, but also a substance which decomposes into small molecules during desorption. This substance may, for instance, belong to the large group of explosives. Substances of this kind are known to excellently bind, by affinity, proteins at their surfaces. The decomposition under the light bombardment blows the protein molecules (and the mediator substance molecules) in gaseous form into the environment. Favorable explosives, e.g. cellulose dinitrate, decompose into water, nitrogen, and carbon dioxide. The nitrogen and water molecules in turn may represent excellent starting molecules for the chain of reactions for chemical ionization described above. The addition of decomposable substances permits to optimize the concentrations of the mediator substances because they no longer must separate the analyte molecules during desorption. It is still favorable to have the mediator substances in much higher concentration than the analyte molecules.

The analyte molecules must be separated from each other during the evaporation process, as otherwise they will immediately form molecule clusters because their low vapor pressure makes this inevitable. The matrix substance must therefore be capable of taking up the analyte molecules and keeping them separate, so that they do not immediately come into contact with each other during the desorption process. Explosives are ideally suited for this task.

The desorption of the sample molecules, i.e. the analyte molecules, the mediator molecules, and the molecules of the explosive, is favorably initiated by bombardment with a light beam from a laser or a laser diode. A continuous laser light beam may be used, but then the focus should be in the micrometer or sub-micrometer range, and the focus should move very fast over the sample to avoid any local overheating. The focus can be moved by moving mirrors, or the sample carrier can be moved accordingly.

On the other hand, the desorption of the analyte molecules may be produced by bombardment with light pulses from a pulse laser or a pulsed laser diode. In this case, the pulse frequency of the desorption light pulses should favorably be sufficiently high to produce a continuous flow of gasified sample material. The desorption usually is performed into a slowly moving inert gas which takes away the plumes of gaseous desorption material. If the speed of inert gas is about 50 millimeters per second away from the sample, and one plume expands into a size of 100 micrometer, then a frequency of 500 Hertz will generate a sequence of plumes touching each other. A continuous rivulet of desorbed material is moving away from the sample carrier plate. By this rivulet of desorbed molecules, a continuous stream of analyte ions is generated once the analyte molecules are ionized by chemical reactions with the reactant ions. In addition, the ion migration by their ion mobility in the electric field towards the inlet capillary mixes the ions from different plumes. The speed of the migration is very different for ions of different mobility causing different migration times from a few milliseconds to a few ten milliseconds. Thus the ions sucked in by the inlet capillary at a given time moment may stem from very different individual laser pulse plumes. A continuous and homogeneous ion current helps in producing high quality mass spectra by most mass spectrometers.

The density of desorbed mediator and analyte molecules in this type of ion source must not be too high for a best cooling effect inside the plume. Fast cooling is required to preserve the analyte molecules in an unfragmented stage. Correspondingly, the laser light conditions have to be carefully selected not to desorb too much material on one hand, but not to desorb only the substances with the highest vapor pressure on the other hand (presumably the mediator substances). A low laser fluence in a large laser light spot diameter produces fractionated distillation; only the high vapor pressure substances are desorbed leaving the analyte molecules behind. This danger can be avoided by modulating the laser light beam profile to show only a few speckles of high intensity. The speckles should have diameters in the range of a few micrometers only or even less. The laser fluence in the speckles is very high causing strong overheating in very tiny spots of the sample with successive rapid expansion of the small volumes of overheated material into a relatively small plumes. This complete evaporation of small sample volumes leaves no room for substance fractionating distillation effects. The overheating in the tiny spots lasts only for a few ten nanoseconds, then rapid cooling takes place by the expansion process on one hand, and by contact with ambient inert gas on the other hand. The speckles can be made to move around on the sample from shot to shot.

The analyte ions generated in this process are drawn towards the opening of the inlet capillary of the mass spectrometer by a suitable electric field, as known from electrospray ionization. They are then sucked into the vacuum system of the mass spectrometer together with surrounding inert gas via the inlet capillary, where they are separated from the gas in a differential pump system by suitable means, such as skimmers or high-frequency ion funnels, before they are then conveyed via known RF ion guides to the mass analyzer, where they are measured as a mass spectrum.

Figure 2:
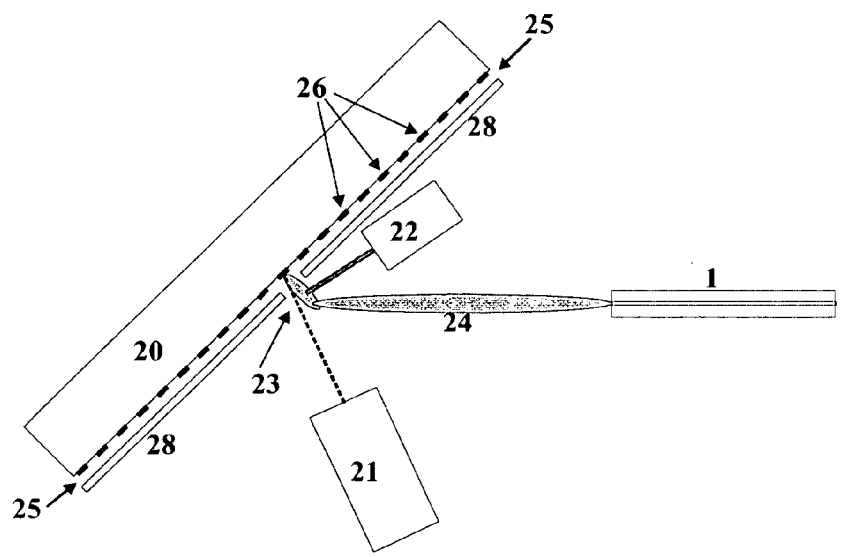
FIG. 2 shows a scheme of the laser desorption ion source in more detail. The movable sample carrier (20) with a plurality of samples (26) is covered by an unmovable shield (28), behind which a low flow of inert gas (25) is fed to the sample under investigation. The laser (21) generates a tiny plume (23), elongated and transported away by the gas stream, in which mediator molecules are photo ionized by the UV laser diode (22). The analyte ions generated by chemical ionization in reactions with the mediator ions are extracted by an electric field and migrate by ion mobility through inert gas along the path (24) to the inlet capillary (1) of the mass spectrometer.

An embodiment of the ion source used for the method of the invention is presented as a rough scheme in FIG. 2. A movable sample carrier (20) carries a multitude of samples (26), consisting at least of biomaterial molecules and mediator molecules. The carrier can be moved to locate one of the samples into the laser focus of the laser (21). The sample carrier (20) is covered by an unmovable shield (28) which protects most of the samples (26), and leads a small gas stream (25) to the sample in the laser focus. The inert gas leaves the space between sample carrier (20) and shield (28) through a hole in the shield (28). The hole allows the laser beam to hit the sample, and the plume (23) to be transported by the gas stream (25) into the radiation beam of the UV laser diode (22). By this irradiation, the mediator molecules inside the plume (23) are converted to reactant ions which in turn ionize the analyte ions. The analyte ions inside the plume (23) are now extracted by an electric field; they migrate through inert gas along the path (24) to the entrance opening of the inlet capillary (1) of the mass spectrometer where they are sucked, together with ambient inert gas, into the vacuum system of the mass spectrometer.

The mass spectrometer of FIG. 1 is a reflector type time-of-flight mass spectrometer with orthogonal ion injection (OTOF), as used for the analysis of ions generated by electrospray. The analyte ions sucked into the inlet capillary (1) together with ambient inert gas, are guided by the ion funnel (8) and the ion guides (9) and (10) through the stack of lens diaphragms (11) to the mass analyzer. The ion funnel (8) and the radio frequency ion guides (9) and (10) serve to get rid of the inert gas on the way through the differential pumping chambers (2), (3) and (4), pumped by the pumps (5), (6), and (7). Ion funnels operated by radio frequency voltages, and radio frequency ion guides are widely known to any specialist in the field. The ion guides can transport ions above a certain mass, this lower mass limit can be used to get rid of the light reactant ions which are no longer used.

The lens diaphragms (11) form a narrow analyte ion beam of almost homogeneous kinetic energy of the ions. Inside the mass analyzer, sections of this beam are pulsed periodically by a pulser (12) into a direction vertical to the injected beam. Within the deflected beam of these flying sections, the ion types of different masses are separated because light ions have a higher velocity than heavy ions. The beam is reflected by the reflector (13) which focuses ions of the same mass but slightly different kinetic energies onto the detector (14). The detector (14), a multi channel plate, converts the ions into a multitude of electrons which finally induce a voltage pulse in the cone (15). Cone (15) is the final piece of a 50 Ohm coaxial cable which transfers the voltage pulses to an amplifier. The amplified voltage pulses, reflecting the original ion current within the mass analyzer, are digitized and stored as a single mass spectrum.

The pulsing of the beam sections is usually repeated with a frequency of about 15 kilohertz, limiting the flight times measured in the spectra to about 66 microseconds. With about 10 kilovolt acceleration in the pulser (12), a mass range of about 5,000 Daltons is achieved. For a higher mass range, the frequency of the pulser has to be lowered. With 15 kilohertz, 15,000 single spectra are measured per second. The ion currents are usually digitized in a rate of two gigahertz, one measurement takes only half a nanosecond. Many single spectra are added, measurement by measurement to form a sum spectrum. Sum spectra can be collected over varying times. Sum spectra can be delivered, for instance, every tenth of a second, or every second, or, if desired, every ten seconds. The lengths of the collection time determines the dynamic measuring range. The dynamic measuring range easily covers four to six orders of magnitude.

The performance of such time-of-flight mass spectrometers depends on the length of the flight paths inside. Even in table-top mass spectrometers, the sum spectra so obtained display a high mass resolving power in the order of R=10,000 to 20,000, a stable calibration of the mass scale, and therefore a high mass accuracy in the order of a few millionths (ppm) of the mass value. Larger mass spectrometers or mass spectrometers with more than one reflector, may achieve sub-ppm mass accuracies for ion signals which are isotope resolved even for molecules in the mass range of 20,000 Daltons.

An ion cyclotron resonance mass spectrometer (known also as Fourier transform mass spectrometer FTMS) can also be used for this purpose. This mass spectrometer has an extremely high mass accuracy to within less than a millionth of the mass value, but far lower dynamic measuring range. The lower dynamic measuring range is a result from a low periodicity in the measurements within this type of mass spectrometer.

As described above, one objective of the invention is to replace the poorly resolved protein profile spectra, with low mass accuracy but high information content, that are produced by time-of-flight mass spectrometers operated in linear mode, by mass spectra that offer a similar wealth of information combined with high mass resolution and high mass accuracy. The procedures provided as preferred embodiments particularly suit this objective. They deliver mass spectra of high mass resolution, with a wealth of ion signals, and offer high mass precision and accuracy.

The various embodiments still offer even more advantages.

Firstly, high-resolution mass spectrometers for external ion generation by electrospray are readily available commercially as fully developed systems. So the development of a mass spectrometer for this inventive method does not require a high-cost development project. If the number of mass spectrometers produced increases considerably as a result of this invention, there may even be a cost reduction for this type of mass spectrometer.

Secondly, laser desorption at atmospheric pressure is simple, and does not require the sample carrier plates to be introduced into the vacuum. The sample carrier plates are simply placed on a moving device, and the analysis can begin. This is a particular advantage for users in medical and microbiological circles who are not accustomed to using vacuum apparatuses.

Thirdly, the ease of use of this type of mass spectrometers and the reproducibility of the mass scales achieved with the invention may even finally introduce mass spectrometers as diagnostic tools into the medical-diagnostic market, once the search for biomarkers has been successful.

The particularly preferred method can, however, be modified in many different ways by a specialist in the relevant field who has knowledge of this invention. Some of these modifications have already been described above, but there are certainly other methods, on the fundamental basis of desorption and post-ionization of analyte mixtures at atmospheric pressure, which can generate the required mass spectra of these analyte mixtures with a high information content.

What is claimed is:

1. Method for acquiring mass spectra of complex analyte mixtures from biomaterial, comprising the following steps:
   (a) providing a high-resolution mass spectrometer capable to analyze ions generated at atmospheric pressure,
   (b) preparing samples containing the analyte mixtures on a sample carrier,
   (c) desorbing sample molecules from a sample on the sample carrier in an inert gas at atmospheric pressure,
   (d) creating reactant ions inside the plume of desorbed sample molecules and thereby ionizing the analyte molecules by reactions with the reactant ions,
   (e) feeding at least a part of the analyte ions into the vacuum system of the mass spectrometer, and
   (f) acquiring high-resolution mass spectra of the analyte ion mixture.

2. Method according to claim 1, wherein the high-resolution mass spectrometer is a reflector type time-of-flight mass spectrometer with orthogonal ion injection.

3. Method according to claim 1, wherein the sample on the sample carrier contains a mediator substance beside the analyte molecule mixture.

4. Method according to claim 3, wherein the mediator substance is selected from the group of matrix substances used hitherto in ionization by matrix-assisted laser desorption.

5. Method according to claim 3, wherein molecules of the mediator substance are transformed into reactant ions by electrons shot into the desorption plume.

6. Method according to claim 5, wherein the electrons are generated by beta radioactivity, by a corona discharge, or by a surface under irradiation.

7. Method according to claim 3, wherein molecules of the mediator substance inside the desorption plume are transformed into reactant ions by photo ionization.

8. Method according to claim 7, wherein the photons for the photo ionization are created by an UV lamp or by an UV laser diode.

9. Method according to claim 1, wherein the sample contains a substance which decomposes into small molecules during desorption.

10. Method according to claim 1, wherein desorption of the analyte molecules is produced by bombardment with a continuous light beam from a CW laser or a CW laser diode.

11. Method according to claim 1, wherein desorption of the analyte molecules is produced by bombardment with light pulses from a pulse laser or a pulsed laser diode.

12. Method according to claim 11, wherein the pulse frequency of the desorption light pulses is sufficiently high to produce a continuous flow of gasified sample material.

13. Method according to claim 12, wherein the pulse frequency of the light pulses is higher than 500 Hertz.

* * * * *